United States Patent
Iversen et al.

(10) Patent No.: US 9,885,665 B2
(45) Date of Patent: Feb. 6, 2018

(54) METHOD, SAMPLE CARRIER, AND DEVICE FOR THE QUALITATIVE AND/OR QUANTITATIVE DETECTION OF PARTICLES IN A FLUID

(71) Applicant: GRUNDFOS HOLDING, Bjerringbro (DK)

(72) Inventors: Kåre Iversen, Langå (DK); Mathis Dahlqvist, Vejle (DK); Christian Guldbæk Smith, Skødstrup (DK)

(73) Assignee: GRUNDFOS HOLDING A/S, Bjerringbro (DK)

(*) Notice: Subject to any disclaimer, the term of this patent is extended or adjusted under 35 U.S.C. 154(b) by 87 days.

(21) Appl. No.: 14/867,364

(22) Filed: Sep. 28, 2015

(65) Prior Publication Data
US 2016/0091435 A1   Mar. 31, 2016

(30) Foreign Application Priority Data
Sep. 29, 2014   (EP) .................................... 14186884

(51) Int. Cl.
*G01N 21/00* (2006.01)
*G01N 21/84* (2006.01)
(Continued)

(52) U.S. Cl.
CPC ........ *G01N 21/84* (2013.01); *B01L 3/502715* (2013.01); *G01N 15/0205* (2013.01); *G01N 15/0227* (2013.01); *G01N 15/06* (2013.01); *G01N 15/1434* (2013.01); *G01N 15/1463* (2013.01); *G01N 15/1475* (2013.01); *G01N 21/0303* (2013.01); *B01L 2200/027* (2013.01); *B01L 2300/0654* (2013.01);
(Continued)

(58) Field of Classification Search
CPC ....... B01L 2200/027; B01L 2300/0654; B01L 2300/0816; B01L 3/502715; G01N 15/0205; G01N 15/0227; G01N 15/06; G01N 15/1434; G01N 15/1463; G01N 15/1475; G01N 2015/0693; G01N 21/0303; G01N 21/84
USPC .................................................. 356/432–448
See application file for complete search history.

(56) References Cited

U.S. PATENT DOCUMENTS 5,292,484 A   3/1994   Kelln et al.
5,726,751 A   3/1998   Altendorf et al.
(Continued)

FOREIGN PATENT DOCUMENTS

| EP | 2 469 264 A1 | 6/2012 |
| WO | 2010/063293 A1 | 6/2010 |
| WO | 2014/094790 A1 | 6/2014 |

*Primary Examiner* — Tri T Ton
(74) *Attorney, Agent, or Firm* — McGlew and Tuttle, P.C.

(57) ABSTRACT

The device serves for the qualitative and quantitative detection of particles in a fluid and includes a light source (1), an optical sensor (2) and a sample carrier (4) which is arranged therebetween and which is for receiving fluid to be examined. The sample carrier is (4) movable relative at least to the sensor (2) and is connectable via a fluid inlet (9) to a conduit (11) for feeding the fluid, and via a fluid outlet (10) to a conduit (12) for the discharge of fluid. The sample carrier (4) is exchangeably arranged in a receiver of the device, so that this sample carrier can be replaced by another one in a rapid and simple manner when the sample carrier (4) is contaminated.

18 Claims, 8 Drawing Sheets

(51) Int. Cl.
  *G01N 15/02* (2006.01)
  *G01N 15/06* (2006.01)
  *G01N 21/03* (2006.01)
  *G01N 15/14* (2006.01)
  *B01L 3/00* (2006.01)
  *G01N 33/18* (2006.01)

(52) U.S. Cl.
  CPC .. *B01L 2300/0816* (2013.01); *G01N 33/1893* (2013.01); *G01N 2015/0693* (2013.01)

(56) References Cited

U.S. PATENT DOCUMENTS

| | | | |
|---|---|---|---|
| 5,731,212 A * | 3/1998 | Gavin | B01L 3/502 356/244 |
| 9,528,944 B2 * | 12/2016 | Bentien | G01N 15/0227 |
| 2003/0058445 A1 | 3/2003 | Fritz et al. | |
| 2006/0228259 A1 | 10/2006 | Samsoondar | |
| 2007/0031289 A1 | 2/2007 | Cox et al. | |
| 2010/0151512 A1 | 6/2010 | Huemer | |
| 2012/0046203 A1 | 2/2012 | Walsh et al. | |
| 2013/0172698 A1 | 7/2013 | Reynolds et al. | |
| 2014/0138260 A1 | 5/2014 | Briman | |
| 2014/0193892 A1 | 7/2014 | Mohan et al. | |

* cited by examiner

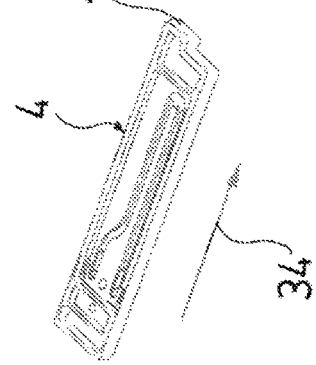
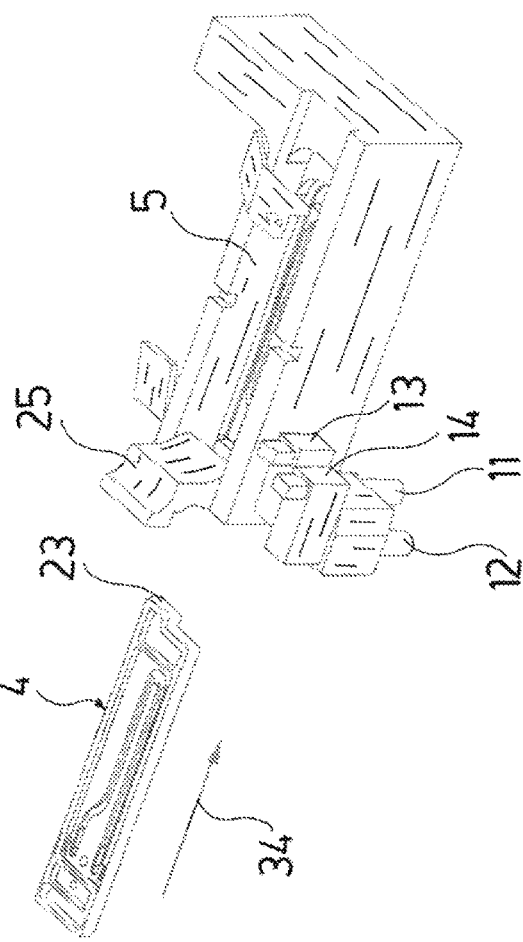
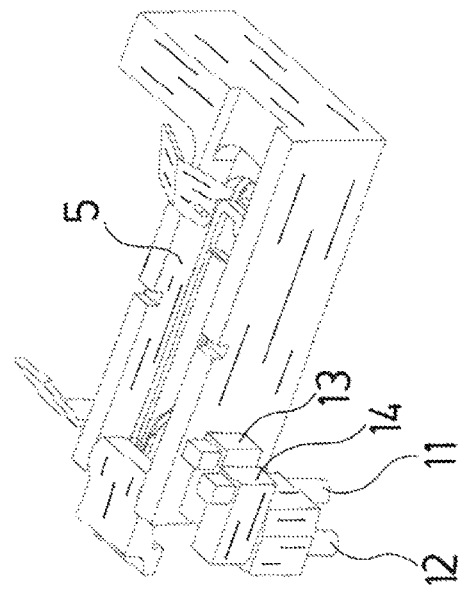

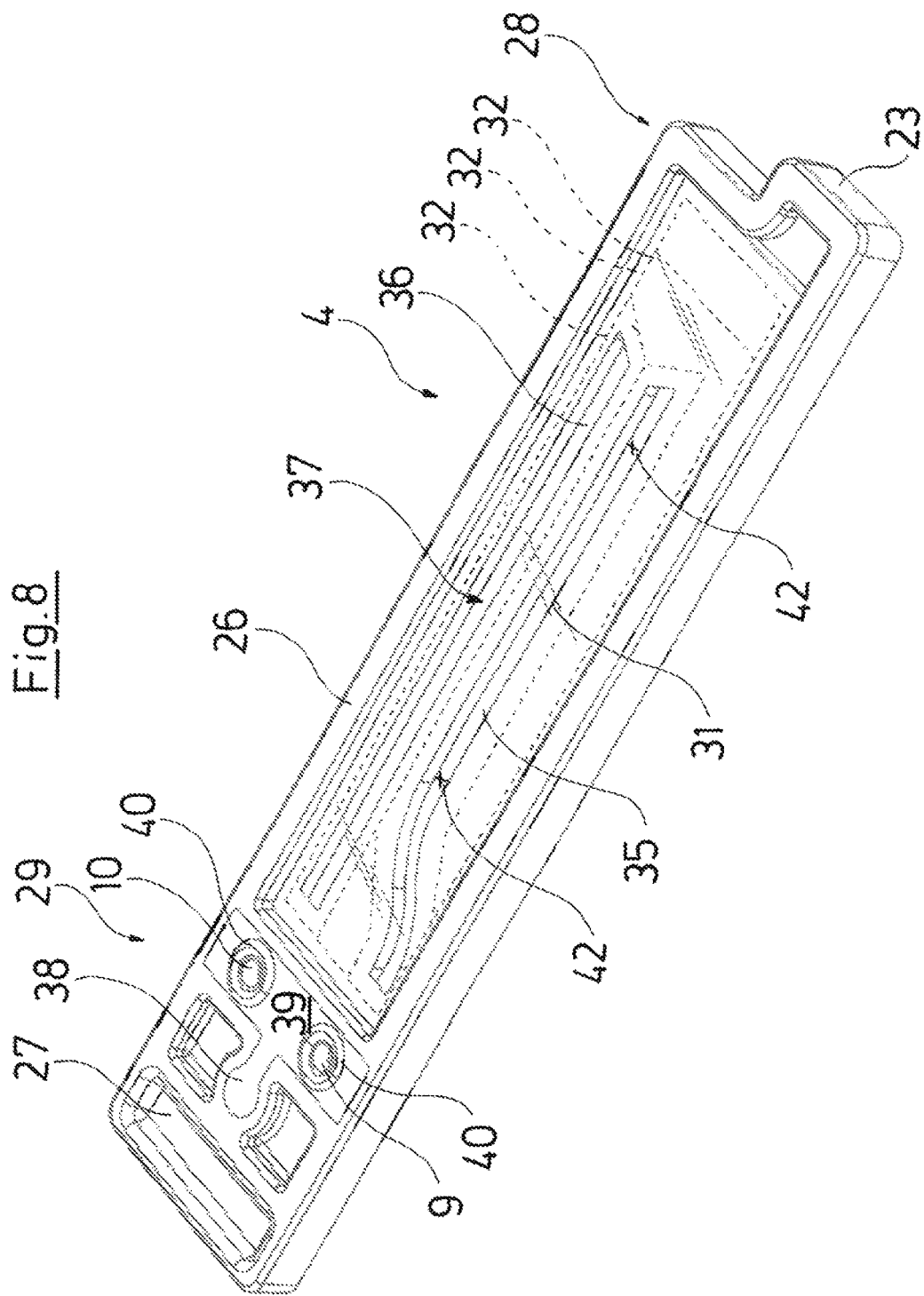

METHOD, SAMPLE CARRIER, AND DEVICE FOR THE QUALITATIVE AND/OR QUANTITATIVE DETECTION OF PARTICLES IN A FLUID

CROSS REFERENCE TO RELATED APPLICATIONS

This application claims the benefit of priority under 35 U.S.C. § 119 of European Patent Application 14 186 884.4 filed Sep. 29, 2014 the entire contents of which are incorporated herein by reference.

FIELD OF THE INVENTION

The invention relates to a device for the qualitative and/or quantitative detection of particles in a fluid, with a light source, with an optical sensor and with a sample carrier which is arranged therebetween and which is for receiving fluid to be examined, wherein the sample carrier is movable relative at least to the sensor and is connectable via a fluid inlet to a conduit for feeding the fluid, and via a fluid outlet to a conduit for the discharge of fluid, and to a method for the operation of such a device, as well as to a sample carrier for such a device.

BACKGROUND OF THE INVENTION

A device of the known type is known from EP 2 469 264 A1. It comprises a light source and an optical sensor, between which a sample carrier for receiving a fluid to be examined is arranged, said sample carrier being movable relative to the sensor and comprising a window, in which the fluid to be examined is arranged and through which one radiates from a light source, so that particles located in the fluid within the window can be detected by way of the sensor. A multitude of sections of the window and of the fluid located therein can be detected by way of a relative movement between the sample carrier and the optical arrangement, so that the type and the number of the particles located within the window in the fluid can be detected after evaluation in the manner described there. Apart from this mentioned document, WO 2010/063293 A1 as well as WO 2014/094790 A1 are yet also referred to with regard to details of the method.

The sample carrier which is only schematically represented in EP 2 469 264 A1, is integrated into a feed conduit and into a discharge conduit, which each via valves are fixedly connected to the sample carrier and the device and via which a fluid exchange can be effected in the sample carrier, for examining different fluid which is to say liquid samples.

Such an arrangement basically has proven its worth, but however requires a regular maintenance, in particular with the continuous monitoring such as is necessary for example for monitoring drinking water. Thereby, the sample carrier at least in the region of the window is not only to be cleaned from the outside but also from the inside, if for example particles have accumulated there, be this in the form of a film of bacteria, algae growth or likewise. The cleaning of the sample carrier is cumbersome, and moreover the device cannot be used during this time.

SUMMARY OF THE INVENTION

Against this background, it is an object of the invention to design a device of the known type, such that a more reliable long-term operation is possible with little maintenance work. Moreover, a correspondingly designed sample carrier is to be provided, as well as a method for operating the device.

According to the invention, the device according to the invention, for the qualitative and/or quantitative detection of particles in a fluid comprises a light source, an optical sensor and a sample carrier which is arranged therebetween and which is for receiving fluid to be examined. The sample carrier is movable relative at least to the sensor and can be connected via a fluid inlet to a conduit for feeding fluid and via a fluid outlet to a conduit for the discharge of fluid. According to the invention, the sample carrier is exchangeably arranged in a receiver of the device.

The basic concept of the present invention, is to design a device, with which the sample carrier itself is provided with conduits for the exchange of the fluid located therein, in a manner such that this sample carrier is exchangeably arranged in the device, thus to provide a separate receiver, from which or into which the sample carrier can be removed or inserted respectively.

Thereby, exchangeable in the context of the invention is to be understood as a preferably tool-free exchange. The sample carrier and the receiver within the device are advantageously arranged such that these are accessible from the outside, which is to say the sample carrier can be exchanged without a disassembly of device parts. The solution according to the invention thus envisages an exchangeable sample carrier, although the exchange of the fluid is typically not effected by the exchange of the sample carrier, but by fluid exchange within the sample carrier, specifically via the feed conduit and the discharge conduit. This, in a further development of the invention does not however exclude sample carriers which are provided and envisaged for the fluid to remain in the sample carrier alternatively also being able to be applied.

The solution according to the invention is advantageously provided for drinking water analysis, but can basically also be applied to all other fields where it is a question of the qualitative and/or quantitative detection of particles in a fluid. Here, cooling water, process water, waste water, liquid chemicals, printers ink and likewise are mentioned merely by way of example. Thereby, particles in the context of the present invention are typically to be understood as bodies of a magnitude in the 100 nm range or upwards, thus for example bacteria, organic or inorganic bodies or other particles. The invention basically is not limited to the particle size, but a natural limitation however results due to the wavelength of the applied light source and of the detecting sensor. Thereby, a light source with an optical a sensor is to be understood as any suitable electromagnetic source with a sensor which is sensitive to this wavelength range, which can also lie outside the visible light region.

The sample carrier is thus designed such that a closed channel is formed between the conduit connections in the sample carrier, said channel at least in sections on two sides which are opposite and away from one another, usefully on the upper side and the lower side, comprising a transparent wall, so that a window which is beamed through by the light source and can be detected by the optical a sensor is formed via a section of the channel Basically, the channel does not need to be closed and it is conceivable for example for it to be open at the upper side, in order for example to permit a degassing of the fluid before the examination. The closed channel in contrast permits a pressure increase during the examination, by which means a degassing and the formation of bubbles which this entails can be prevented.

Shut-off means are provided, in order to be able to control the feed and discharge of fluid into and out of the sample carrier. Thereby, at least one shut-off valve is provided in the feed conduit, preferably however a further one in the discharge conduit, in order to be able to close off the channel within the sample carrier, so that a flow in the channel during the examination is ruled out and thus a calming of the fluid and the particles contained therein is ensured.

It is particularly advantageous if both conduits, thus the feed conduit and the discharge conduit run out into the sample carrier from below and specifically preferably next to one another in the insertion direction. Such an arrangement is advantageous, since then any fluid remains adhering to the connections on the sample carrier can drip away downwards into the open, without the danger of the fluid collecting in the receiver or distributing outside on the sample carrier.

Advantageously, the light source is arranged on one side of the sample carrier, and the optical sensor on the other side of the sample carrier, and specifically the optical sensor above the sample carrier and the light source below, within the device. Deposits on the sensor are avoided in a natural manner by way of this. Advantageously, within the device, the sample carrier is arranged in a stationary manner and the optical device consisting of the light source, sensor and, as the case may be, further optical components, is movably arranged to the sample carrier, and specifically in a stepwise manner, so that a movement of the sample carrier and thus of the fluid located therein or the particles located therein, can be avoided between the individual detection procedures, since the detection of particles in the fluid can only be effected with a standstill of the fluid.

It has been found to be particularly advantageous, to arrange the optical axis of the light source and of the optical sensor, and, as the case may be, further optical components, at an angle between 4° and 8° to the perpendicular through-beaming direction through the sample carrier and to move these optical component in this position in a stepwise manner along the sample carrier.

According to a preferred design, the device is designed such that means are provided between the receiver and the sample carrier, which permit a conductive connection to the fluid inlet and/or to the fluid outlet only when the sample carrier is arranged in its designated position in the receiver. Preferably, the means are designed such that the conductive connection (line connection) to the fluid outlet as well as the conductive connection to the fluid inlet can only be formed in this designated position.

This can advantageously be achieved by way of a first switch being provided, which switches on reaching the designated position of the sample carrier in the receiver. This can be a microswitch which operates electrically or a mechanical switch which controls the valve release.

According to a further development of the invention, positive fit means are provided between the receiver and the sample carrier, in order to ensure that the sample carrier can only be inserted into the receiver in the position envisaged for this. Such positive-fit means can be formed in an asymmetrical profile of the sample carrier and receiver, or for example by end-side projections which can be introduced into a corresponding receiver-side recess only in one position, or in another suitable manner, if the sample carrier is to be insertable into the receiver.

According to a further development of the invention, a preferably pivotable bar (lock) is provided, with which the sample carrier can be fixed with a positive fit in its designated position in the receiver, in order to ensure that the sample carrier remains in its designated position in the receiver also during the detection. Such a bar can be pivoted after the insertion of the sample carrier into the receiver, and thus firmly fix the sample carrier in the receiver. Thereby, a second switch is advantageously provided, which detects the locking position of the bar and which can likewise be connected into the control for the conductive connection to the fluid inlet and/or fluid outlet, in order not only to ensure that a conductive connection is only effected when the sample carrier is in its designated position in the receiver, but moreover only when this is also locked in this position. This switch can also be an electrical microswitch or a mechanical switch, which is coupled to the valve control.

The sample carrier for the device according to the invention advantageously comprises a carrier frame which is closed off in each case by a transparent plate at two sides, preferably at the upper side and the lower side (with respect to the designated position in the receiver). Such a sample carrier can be manufactured inexpensively of plastic, wherein the frame on the one hand ensures a stable construction of the sample carrier, and on the other hand can at least laterally delimit the channel formed within the sample carrier. The transparent plates can advantageously likewise consist of plastic and be connected to the frame with a positive fit.

The transparent plates are advantageously set back with respect to the peripheral frame part, in order to prevent these plates from being scratched on inserting or removing the sample carrier into and out of the receiver respectively. Thereby, the frame part is advantageously designed shouldered inwards, thus where the transparent plates are arranged, so that the plates in each case are integrated into a recess which is formed by the frame and which is deeper than a thickness of a plate.

Advantageously, the sample carrier is designed such that with the designated positioning in the receiver, the fluid inlet and the fluid outlet are arranged on the lower side, and specifically preferably next to one another in the insertion direction. Moreover, the fluid inlet and fluid outlet should be arranged as close as possible to the entry of the receiver, so that any adhering water droplets do not remain in the device on pulling out, but are pulled out with the sample carrier in the shortest path. The arrangement next to one another has the advantage that one can reliably rule out fluid from the inlet coming into contact with fluid from the outlet and vice versa. It is particularly useful with the arrangement of the connections next to one another, to provide at least one channel-forming rib between the fluid inlet and the fluid outlet, within the sample carrier, said rib preferably forming a part of the frame. A channel then arises between the fluid inlet and the fluid outlet and this channel on the one hand is delimited by the frame and on the other hand by the rib. This channel is deflected at the end of the same carrier by 180°, thus runs to both sides of the rib. One the one hand the line connection between the inlet and the outlet is ensured by way of this channel guidance which practically creates two channels which are arranged next to one another and connected to one another at the end side, and on the other hand a further examination field which can be used is formed.

According to a further development of the invention, a projection can be provided at the insertion side, thus at the side with which the sample carrier is inserted into the receiver, and this projection is arranged out-of-center and forms a positive fit means for positioning by way of it engaging into a corresponding recess at the end of the receiver, in order to ensure the designated position of the sample carrier within the receiver. Alternatively, the sample carrier and the receiver can have a cross-sectional profile which permits the insertion only in the designated manner.

The frame of the sample carrier can advantageously be designed as a plastic injection molded part, wherein the transparent plates are firmly and sealingly connected to the frame with a material fit, which is to say, be way of bonding or welding. A weld connection is thereby to be preferred, but assumes that the components can be welded to one another.

Sealing means are advantageously provided, in order to ensure a tight or sealed connection of the sample carrier to the conduit connections located within the receiver of the device. It is particularly advantageous with regard to manufacturing technology, if the sample carrier in the region of the inlets and outlets comprises a recess, typically a surfaced deepening in this side of the frame part, said deepening is filled out with an elastic and seal-forming plastic, for example silicone. This plastic in particular can be annularly elevated in the region of the connections, so that it is ensured that these elevations bear in a sealing manner around the respective conduit connections in the receiver after insertion of the sample carrier into the receiver.

According to a further development of the invention, a grip piece which is preferably arranged at the end of a narrow side and forms part of the frame is provided on the sample carrier, in order to ensure a possible tool-free handling of the sample carrier on inserting into the receiver and withdrawal from it. Such a grip piece can be gripped between the finger and thumb and be accordingly manipulated.

It is particularly advantageous if the sample carrier has an essentially longitudinally extended and flat cuboid or parallelepiped shape, wherein the flat sides are provided with the transparent plates, and the longitudinally extended sides are arranged in the insertion direction. Hereby, the sample carrier can be inserted into the receiver in a pin-like manner, without the danger of a jamming or canting, wherein the longitudinally extended shape ensures an adequately long measurement path within the channel.

According to an advantageous further development of the invention, the closed channel on the inner side, at least in the region which is envisaged for the optical detection of fluid, and there at least on the inner side of the transparent wall, is provided with a coating and/or a surface structuring which prevents, reduces or at least delays the formation of deposits. The coating and/or surface structuring can be dependent on the fluid for which the sample carrier is envisaged. The formation of algae is to be prevented with water for example, but also of other deposits such as bacteria, chalk or likewise. Such a coating can for example be hydrophilic or hydrophobic in nature. The surfaces can have microstructures which render the clinging of deposits more difficult. One can also envisage structured surfaces in combination with coatings. Thus, for example, acrylates, silanes or fluoropolymers and likewise can be used as coatings, as this is known per se.

Moreover, the device itself can be equipped with means for cleaning, be it by way of flushing in intervals with an increased pressure and increased flow speed via a pump of the sample carrier, or by way of an ultrasound exciter being provided, which in particular affects the transparent walls of the sample carrier for the purpose of cleaning. A cleaning device which for example flushes the sample carrier at intervals with a cleaning fluid or a cleaning gas such as ozone for example can also be provided.

Advantageously, the sample carrier in the region which is provided for the optical detection of fluid comprises at least one marking, and specifically preferably between the transparent walls, in particular on an inner side of a wall. Such a marking can be used for the calibration of the optical device, and it can moreover serve to align the autofocus of the optical device to the desired plane in the sample carrier. Markings can also be provided at the beginning and the end of the measurement window and thus mark the region of the window which is envisaged for the optical detection of the fluid. Such a marking can also be effected by engraving or print on one of the transparent plates. The marking is advantageously attached close to the sensor, thus on the inner side of the transparent plate which is closest to the sensor.

The sample carrier and receiver can be designed within large ranges with regard to dimensions and proportions, which is definitely also dependent on the fluid to be examined. If waste water or likewise is to be examined, then larger channels are necessary than with the testing of service water. However, in a multitude of the cases it has been found to be advantageous if the closed channel in the sample carrier, in the region which is provided for the optical detection of the fluid, preferably has a roughly rectangular channel cross section whose width is greater than its height in the perpendicular through-beaming direction. Thereby, the ratio of the width to the height should preferably be 1.5 to 3, thus the channel cross section be 1.5 to 3 times as wide as it is high. Thus, for example, the channel width can be 3 mm and the channel height 1.5 mm for testing drinking water. The flatter the channel, the lower are the reflections within the channel, in particular within the fluid. The thermally induced movement within the fluid in the sample carrier increases with an increasing channel height, at least if the illumination is effected from below and the sensor is arranged at the top, which is preferred, since the temperature difference between the lower side and the upper side of the sample carrier becomes greater. This however is not desired, since the fluid is to be quasi stationary on detection. It is advantageous if the frame of the sample carrier, thus all regions which do not need to be designed in a transparent manner, have an as light-absorbing as possible surface, are preferably black, in order to keep the reflections within the sample carrier low.

The method according to the invention, for detecting particles in a fluid with a device according to the invention, envisages the sample carrier firstly being brought into the envisaged position in the receiver of the device, whereupon in a first step, the fluid to be examined is introduced into the sample carrier via the feed conduit, whereupon in a second step the discharge conduit is shut-off, and the feed conduit is closed in a third step after the build-up of pressure within the sample carrier, whereupon a dwell time is waited and the optical detection of the sample is effected in a fourth step. This method is particularly advantageous since a degassing of the fluid is prevented, at least slowed, due to the build-up of pressure within the sample carrier, so that an undesired formation of bubbles is suppressed. The dwell time serves for arranging the particles within the fluid in a quasi stationary manner. If particles such as bacteria are to be detected for example, then as a rule a dwell time of about one minute is sufficient, in order to ensure a quasi stationary arrangement of bacteria within the fluid. If in contrast particles as are formed due to contamination such as dust, sand and likewise are to be detected, the dwell is to be selected longer as the case may be, in particular with those particles whose specific weight is significantly larger or smaller than that of the carrier fluid. Here the dwell time is selected such that the particles since can sink to the base or floor of the sample carrier or can rise to the surface.

In a fifth step, the feed conduit and the discharge conduit are opened after the optical detection, whereupon the fluid located in the sample carrier is replaced, which is to say rinsed out and the cycle is repeated beginning in the second step, since the sample carrier according to the invention is typically designed for multiple use. Usually, the sample carrier can be used for a long time. Only when deposits or other contamination render the detection of particles more difficult or even impossible, is the sample carrier replaced, wherein this can be effected by way of opening the bar and a simple withdrawal and replacement by a new sample carrier and subsequent closure of the bar, thus by untrained personnel.

The invention is hereinafter explained in more detail by way of one embodiment example represented in the drawing. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

BRIEF DESCRIPTION OF THE DRAWINGS

In the drawings:

FIG. 3a is a simplified perspective representation of the sample carrier;

FIG. 3b is a simplified perspective representation of the receiver;

FIG. 3c is a simplified perspective representation of the receiver with the sample carrier;

FIG. 8 is a perspective representation of the sample carrier from the bottom.

DESCRIPTION OF THE PREFERRED EMBODIMENTS

Figure 1:
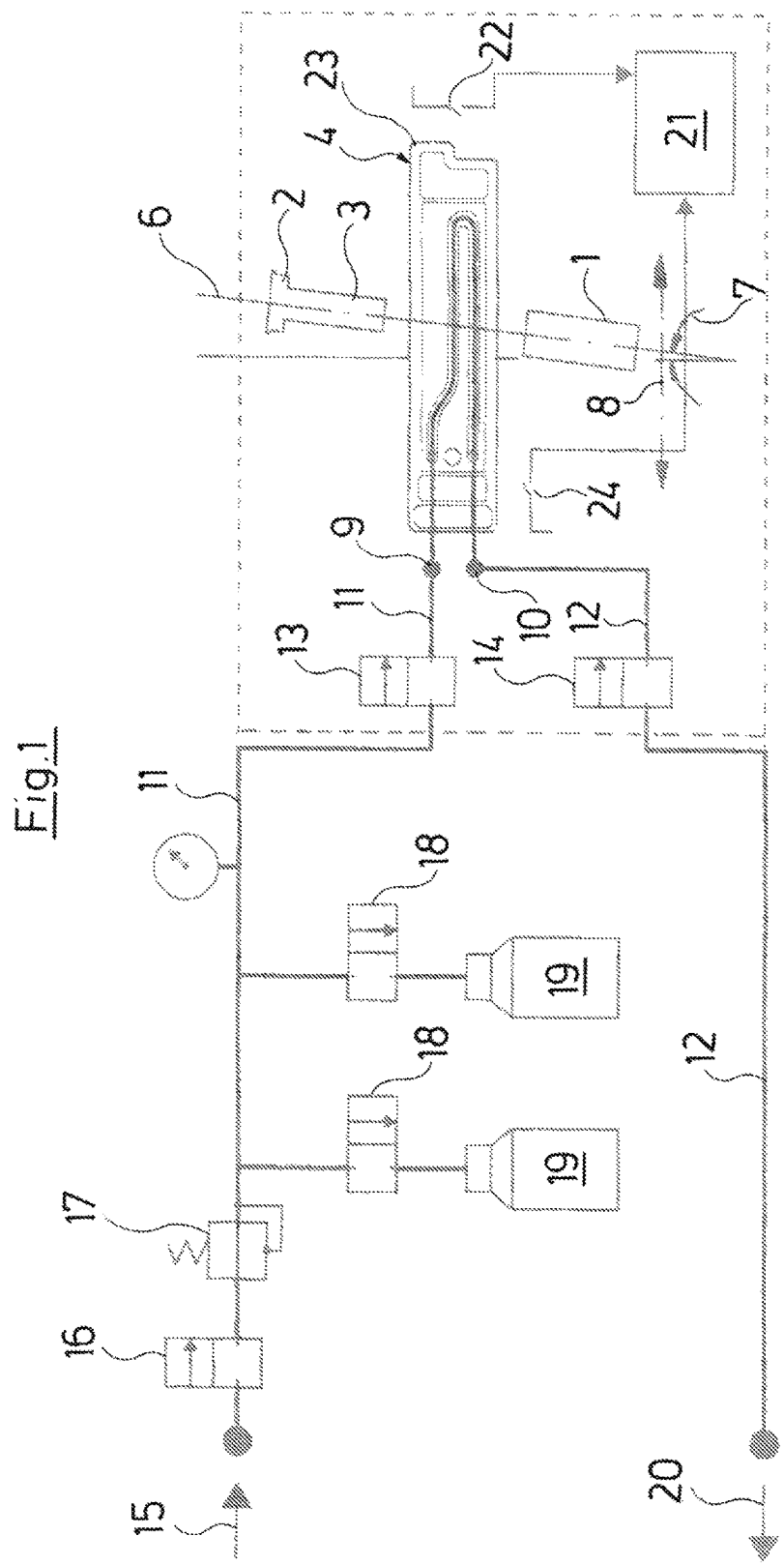
FIG. 1 is a schematic representation showing the construction of the device of the invention.

Referring to the drawings, the essential elements of the device for the qualitative and quantitative detection of particles in a fluid are represented in FIG. 1, wherein the core of the device is formed by the frame represented by interrupted lines, and the remaining components, although belonging to the device, however only belong to the periphery, so that they do not necessarily need to be spatially connected to the device, which is to say arranged in a common housing.

Figure 2:
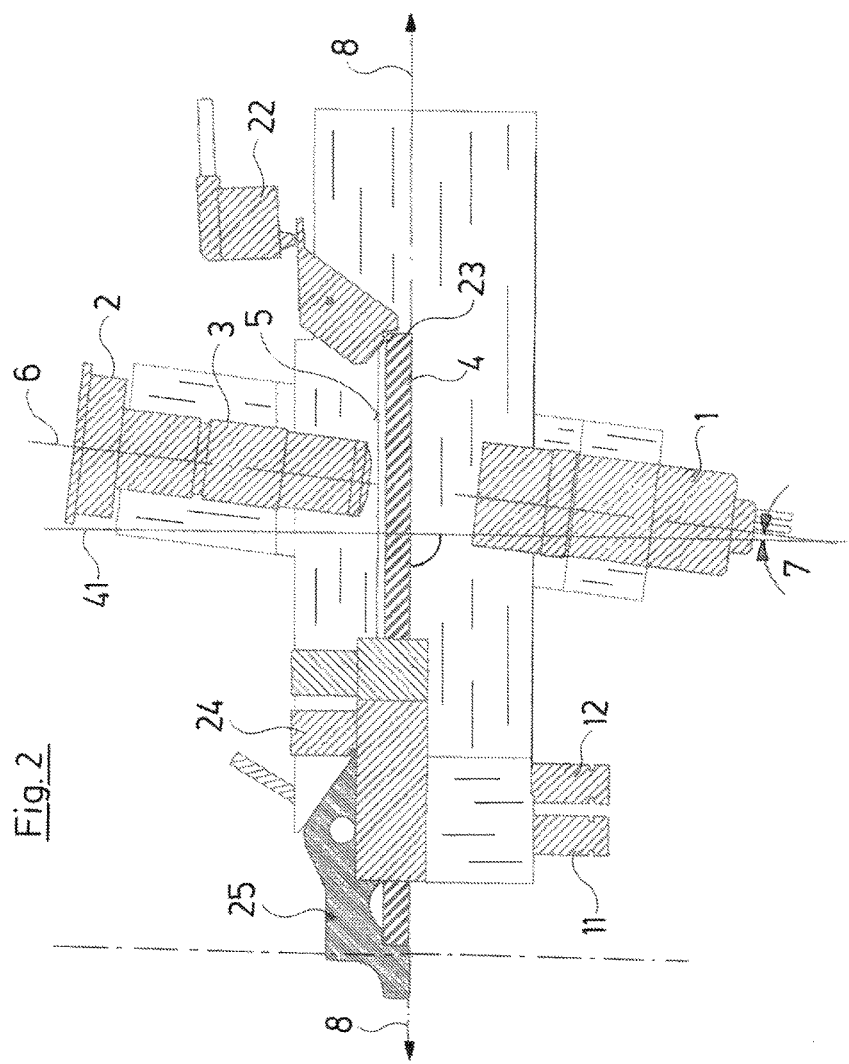
FIG. 2 is a schematic sectioned representation showing the receiver of the device with a sample carrier inserted therein.

The essential elements of the device are an optical device with a light source 1, with an optical sensor in the form of a CCD sensor 2 and with imaging optics 3 which are arranged in front of the latter. A sample carrier 4 passes through this optical device in the region between the light source 1 and the optics 3, and is applied in a receiver 5 of the device, and the fluid to be examined is located in this sample carrier. The sample carrier 4 in FIG. 1 is represented rotated by 90° about a sample carrier longitudinal middle axis for purpose of a better overview. The sample carrier 4 is arranged such that the window of the sample carrier 4, which is described in more detail further below, and through which the fluid is visible from two sides, is arranged between the light source 1 and the optics 3 of the optical sensor 2. The sample carrier 4 is intersected by the optical axis 6 of the optical device and specifically not perpendicularly (the perpendicular through-beaming direction 41 is represented in FIG. 2), but at an angle 7 of 6° in the embodiment shown. This optical device can be moved by way of a stepper motor along the receiver 5 with the sample carrier 4 located therein, so that another part of the fluid to be examined gets into the examination field of the optical device with each displacement step. The displacement device is characterized in FIGS. 1 and 2 at 8.

The sample carrier 4 comprises a fluid inlet 9 and a fluid outlet 10 which when the sample carrier 4 is arranged in its designated position within the receiver 5, are connected to a feed conduit 11 and to a discharge conduit 12 respectively, within the device. A shut-off valve 13, 14 is arranged in each case within the conduits 11 and 12, close to the fluid connections 9 and 10. The feed conduit 11 in the shown embodiment example according to FIG. 1 connects to a service water conduit 15. The feed conduit is connected via a first shut-off valve 16 and a pressure reduction valve 17 and the shut-off valve 13 to the fluid inlet 9. Sample holders 19 which permit a sample withdrawal by way of a container are connected to the conduit 11 via two shut-off valves 18 in the represented embodiment example. The discharge conduit 12 runs out in a run-off conduit 20.

The optical detection procedure including the stepwise movement of the optical device is controlled by a control and regulation device 21 which also includes the microprocessor, in which the evaluation is effected.

The device comprises a position device or position means comprising a first switch 22 which is switched by an face-side projection 23 arranged out-of-center at the introduction-side end of the sample carrier 4, since the sample carrier 4 is exchangeably arranged within the receiver 5, which means to say can be withdrawn and replaced by another sample carrier 4 in a tool-free manner. This switch 22 is only closed when the sample carrier 4 is seated in its designated position in the receiver 5, in which connections 9 and 10 are connected to the conduits 11 and 12. A second switch 24 is moreover provided, and this is switched by a pivotable bar 25, and specifically when the bar 25 is located in the position represented in FIG. 2, in which it secures the sample carrier 4 in the receiver 5 in the designated position with a positive fit. These switches 22 and 24 are connected to the control and regulation unit 21 and ensure that the optical detection of the sample is only effected when these switches are closed, which means to say the sample carrier 4 is arranged in its designated position in the receiver 5 and is secured in this position by the bar 25. The control and regulation unit 21 moreover by way of the switches 22 and 24 ensures that the valves 13 and 14, with which the feed and discharge of fluid to the sample carrier 4 is effected, can only be opened when the sample carrier is in its designated position and thus connections 9 and 10 are connected to the corresponding connections of the conduits 11 and 12 within the receiver 5.

Figure 4:
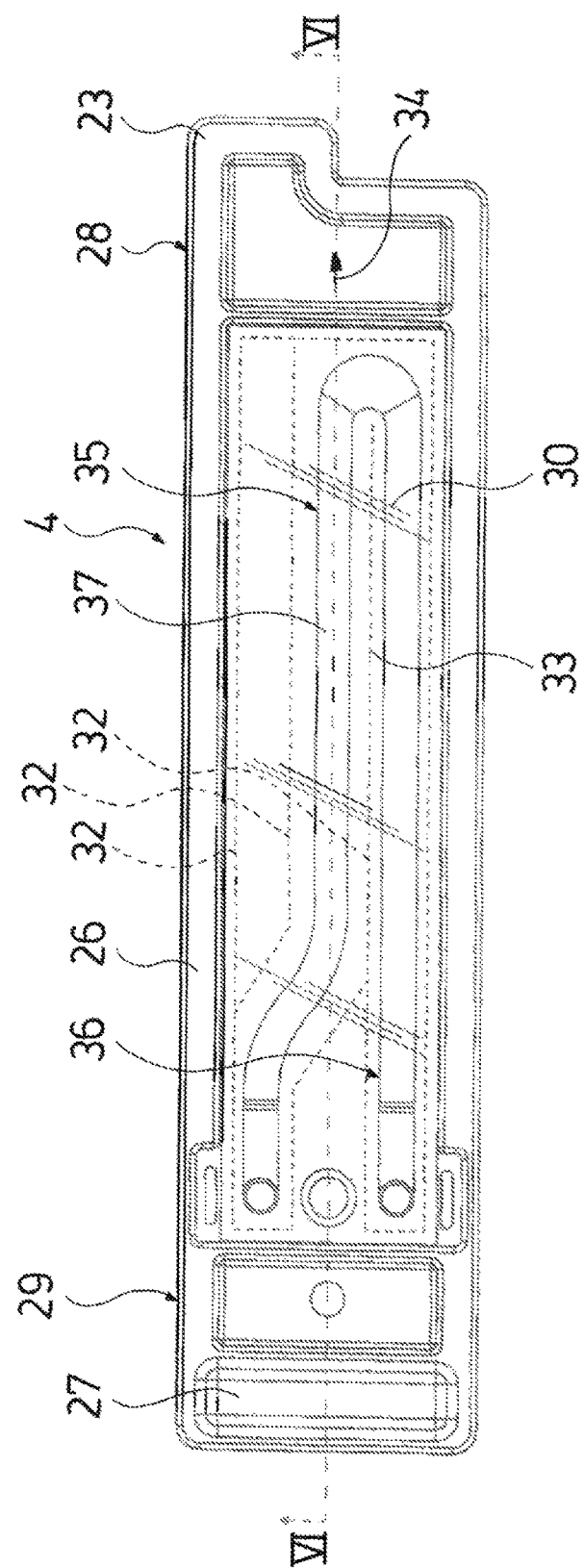
FIG. 4 is a plan view of the sample carrier.
Figure 5:
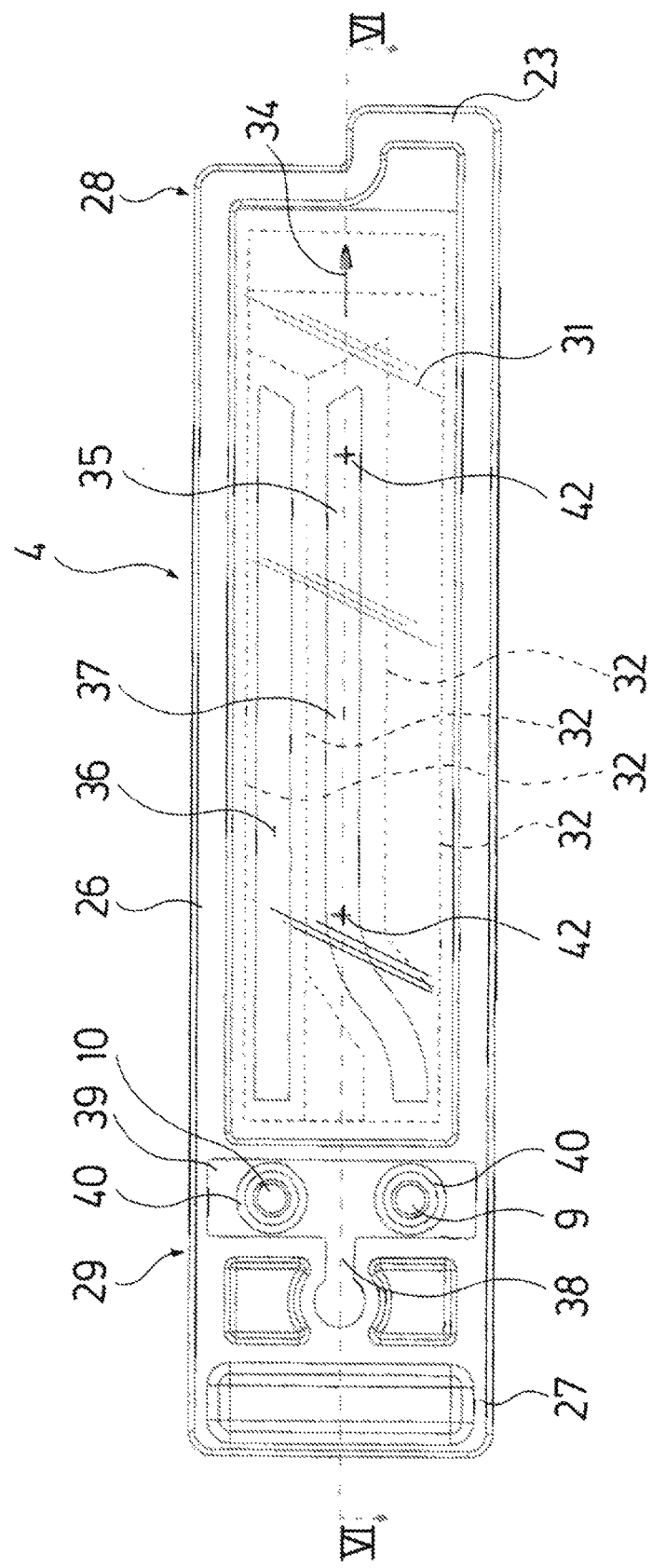
FIG. 5 is an underside view of the sample carrier.
Figure 6:
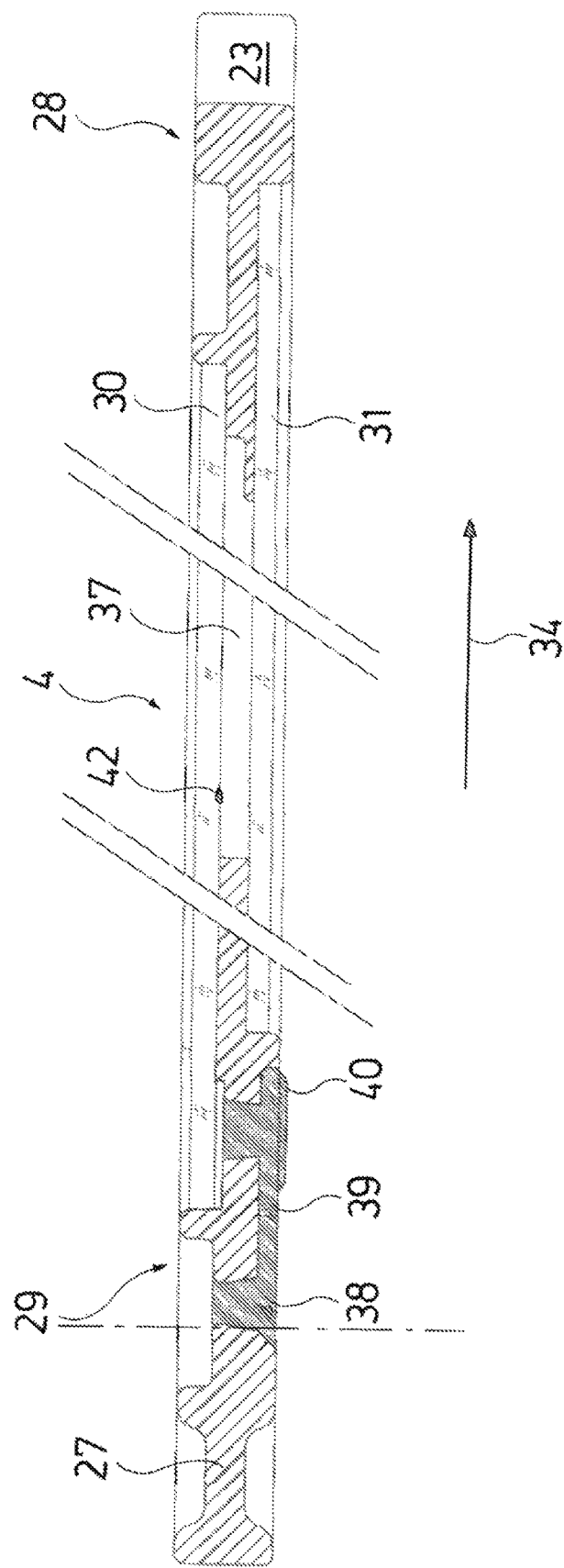
FIG. 6 is a sectional view along the section line VI-VI in FIG. 4 or VI-VI in FIG. 5.
Figure 7:
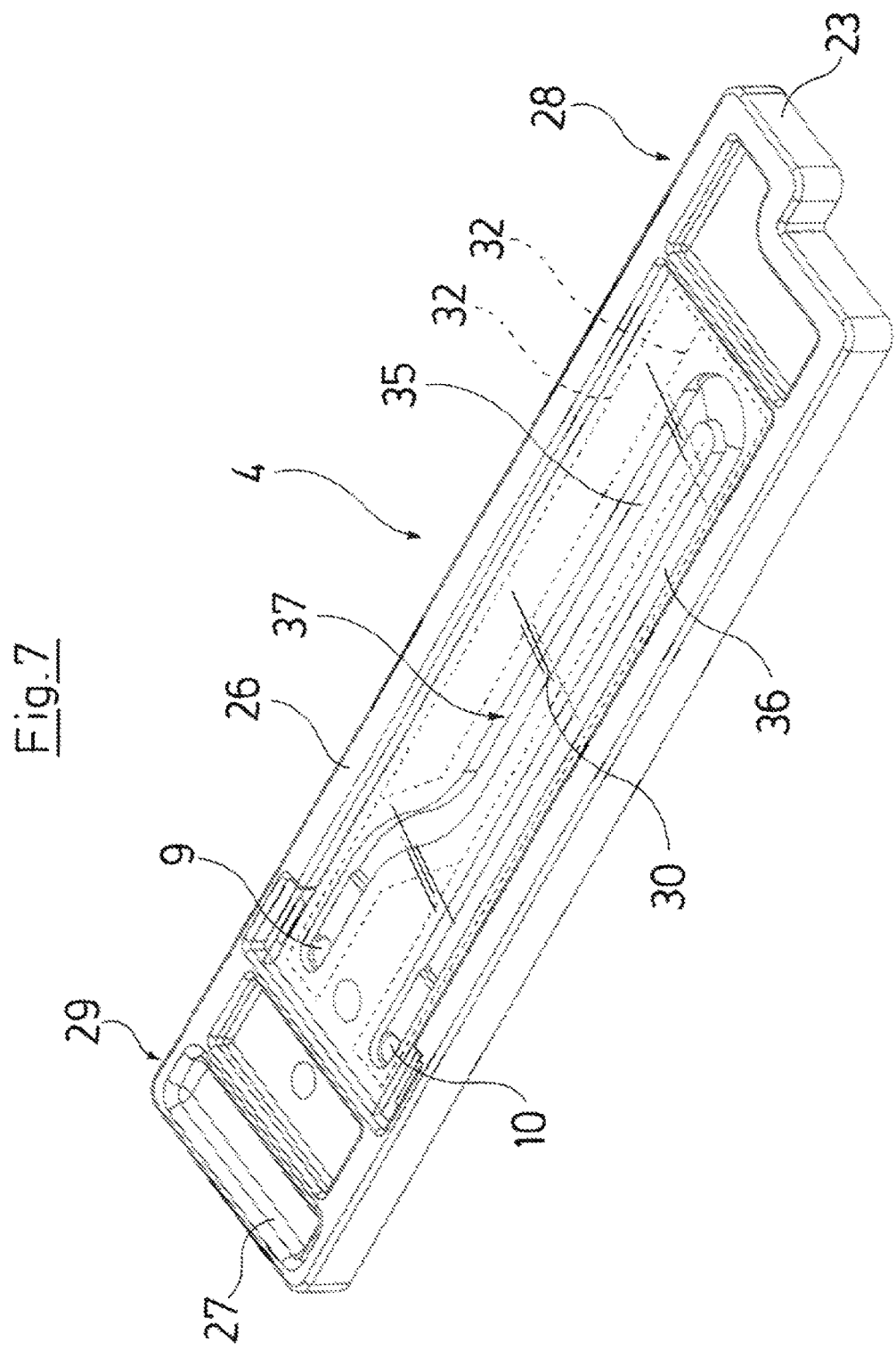
FIG. 7 is a perspective representation of the sample carrier from the top.

The sample carrier 4 has an essentially longitudinally extended, flat cuboid shape and at the insertion-side end is provided at the face-side with the projection 23, said projection engaging into a corresponding end-side recess in the receiver 5 and ensuring that the sample carrier 4 can only be inserted completely into the receiver 5 in the position, in which the projection 23 seen from the top lies to the left of the longitudinal middle line and in the section line VI-VI represented in FIGS. 4 and 5. One can make do without this projection 23 if the cross section is not designed in a rectangular manner, as with the embodiment example, but for example in a trapezoidal or asymmetrically triangular manner, and the receiver has a corresponding cross section, so that an insertion is only possible in an unambiguously defined position, which represents the designated position when the sample carrier 4 has reached the end of the receiver 5.

The sample carrier 4 comprises a peripheral frame 26 which forms the longitudinal sides as well as the face-sides and the projection 23, and well as a grip part 27 at the other end. The frame 26 is designed as a plastic injection molded part and determines the outer contour of the sample carrier 4. The frame 26 between an end-part 28 which has the projection 23, and an end-part 29 which has the grip part 27 comprises a inward step to both flat sides of the sample carrier 4, thus to the upper side and to the lower side in the designated position. This step forms a frame for a window which is formed by the inwardly stepped part of the frame 26 and two discs 30 and 31 which are transparent, are integrated therein on the upper side and lower side, consist of plastic and are unreleasably fixedly and sealingly connected to the frame 26 with a material fit by way of welding. The weld seams are characterized at 32 in the figures. The step of the frame 26 to the inside is selected such that the upper disc 30 and the lower disc 31 are arranged in the frame 26 in a returning manner which means they are always arranged at a distance to the receiver on insertion of the sample carrier 4 into the receiver 5, and thus cannot be loaded, in particular cannot be scratched, during the insertion or withdrawal procedures. In the present embodiment example, the discs 30 and 31 are connected to the frame 26 by way of laser welding. The frame 26 is thus light-absorbing, here is black. Alternatively, such a connection can also be effected by way of ultrasound welding if a laser welding is not possible.

The frame 26 within the window, thus in the region between the discs 30 and 31, comprises a longitudinal rib 33 which forms two connected channels between the fluid inlet 9 and the fluid outlet 10. The inlet 9 and the outlet 10 are arranged on the lower side of the sample carrier 4 and are arranged next to one another in the insertion direction 34. This longitudinal rib 33 ends at a distance to the end part 28, so that a connection of the two channels is formed there. A channel 37 is formed by way of this, and this channel, as is particularly clearly visible in the FIGS. 4 and 5, runs from the fluid inlet 9, firstly a bit in the longitudinal and insertion direction 34 of the sample carrier 4, then obliquely to the middle merges into a longitudinally extended channel section 35, is led close to the end-part 28 by 180°, in order to then merge into a longitudinally extended channel section 36 which runs in the longitudinal direction of the sample carrier in a straight line up to the fluid outlet 10. Thereby, the rib 33 and the steps on the other channel side form the frame-side delimitation of the channel 37 which is otherwise delimited by the discs 30 and 31 on the upper side and lower side. Thereby, the channel section 35 lying in the middle of the sample carrier particularly serves for the optical set-up for the detection of particles within the fluid, whereas the channel section 36 serves for leading back to the fluid outlet 10. As is evident by way of FIGS. 4 and 5, the discs 30 and 31, directly next to the channel 37 are welded to the longitudinal rib 33 or to the stepped region of the frame 26. This on the one hand serves for increasing the stability of the sample carrier and on the other hand for providing the channel with the necessary pressure-resistance, so that the forces acting on the discs 30 and 31 when the channel 37 is subjected to pressure, at least partly can be accommodated by the frame.

The frame 26 on the lower side is designed in a set-back manner, in the region of the fluid inlet 9 and the fluid outlet 10, so that a surface which is sunk with respect to the outer contour of the frame 26 results, and this surface encompasses the fluid inlet 9 and the fluid outlet 10 as well as moreover a web-like region 38. This set-back surface is injected out with a soft-elastic plastic, wherein the web-like region 38 serves essentially for a secure fixation, whereas the region around the fluid inlet 9 and the fluid outlet 10 is designed as a peripheral seal which projects downwards with respect to the contour of the frame 26. This elastic material which in the embodiment example consists of silicone, forms peripheral annular seals 40 around the respective inlets and outlets 9, 10, and on inserting the sample carrier 4 into the receiver 5, these seals serve for connecting the inlet 9 and the outlet 9 to the respective conduit connections in the receiver 5 in a tight manner and sealing them off, on reaching the designated position.

With an upwardly pivoted bar 25, a sample carrier 4 is inserted in the direction 34 into the receiver 5 of the device until the projection 23 in the end-side recess lies within the receiver 5, the bar 25 is then pivoted downwards and the sample carrier 4 is secured in the receiver 5 with a positive fit, for operation of the device. In this position, the first switch 22 is closed by the projection 23, the second switch 24 is closed by the pivoted-down bar. It is then ensured that the sample carrier 4 is in its designated position in the receiver 5, in which position the fluid inlet 9 and the fluid outlet 10 at the lower side of the sample carrier 4 are aligned with the respective conduits 11 and 12 in the receiver 5 and are sealingly connected to these conduits via the annular seals 40. From now, the release of the device is effected by the control and regulation unit 21, which is to say that the valve 16 and the valves 13, and 14 are activated to open, so that the service water to be examined flows via the service water conduit 15 into the device, whereby a sample can be tapped in the container 19, by opening one of the shut-off valves 18 as the case may be, if for example it has been ascertained that the bacterial content of the examined fluid is too high. The pressure of the service water conduit 15 which for example is seven bar is reduced to two bar by way of the pressure reduction valve 17. The service water via the valve 13 and the conduit 11 gets to the fluid inlet 9 of the sample carrier 4, flows there through the channel 37 up to the fluid outlet 10 and from there into the discharge conduit 12 through the shut-off valve 14 to the run-off conduit. 20. For particle detection, the valve 14 is firstly closed, until a pressure for example of two bar has built up in the whole system, which is to say also in the channel 37 of the sample carrier 4. The shut-off valve 13 is then closed and a dwell time is waited, until the fluid in the channel 37 and in particular the particles located therein have calmed, thus are quasi stationary. Then a section of the channel 37 is detected with the optical device by way of the optical sensor 2 and is evaluated with respect to the particles located therein by way of the control and regulation unit 21. The optical device is then displaced by a step in the displacement direction 8 by way of the stepper motor, whereupon a further optical a detection procedure (scan) is effected, and this being the case until the desired number of scan procedures over the length of the channel 37 has been effected. The optical device is subsequently retracted and the valves 13 and 14 opened, in order to exchange the fluid located in the sample carrier.

A multitude of fluid samples can be detected with regard to the particles located therein in this manner, and this being the case in a qualitative manner as well as quantitative manner, which means that by way of the evaluation electronics in the control and regulation unit 21, on the one hand one can ascertain as to what particles it is a case of, for example bacteria or inorganic contamination. On the other hand one can determine in which quantity these are present.

If it is ascertained by way of the optical device that such an amount of deposits has formed in the sample carrier, be they organic coating or other particles, that the function is compromised, wherein this can likewise be effected in an automated manner, then this can be displayed by a display on the device. The sample carrier 4 must then be replaced by another sample carrier, by way of the bar 25 being opened, the sample carrier 4 located in the receiver 5 being pulled out and being replaced by another one.

A multiple use of one and the same sample carrier 4 is envisaged in the present embodiment example by way of the fluid in the sample carrier being exchanged. The sample carrier 4 can be designed for the one-off use if suitable check flaps or valves are provided in the fluid inlet 9 and the fluid outlet 10, so the fluid examined in the sample carrier is also removed with the withdrawal of the sample carrier and can be mounted within the sample carrier 4 quasi as a sample container.

Two markings 42 are provided within the sample carrier 4, and specifically in the region of the window, and specifically where the closed channel 37 is provided for the optical detection of the fluid, thus in the region of the channel section 35, and specifically on the inner side of the upper disc 30 which is closer to the sensor 2 than the lower disc 31. These markings here characterise the measurement path, i.e. within which the optical device travels the sample carrier 4, in order to examine the fluid located in the channel section 35. Thereby, the markings 42 serve for the calibration of the optical system as well as for the autofocus of the optical system, in order to focus onto the plane, in which the fluid to be examined is located.

While specific embodiments of the invention have been shown and described in detail to illustrate the application of the principles of the invention, it will be understood that the invention may be embodied otherwise without departing from such principles.

APPENDIX: LIST OF REFERENCE NUMBERS 1 light source
2 optical sensor
3 optics
4 sample carrier
5 receiver
6 optical axis
7 angle
8 displacement direction
9 fluid inlet
10 fluid outlet
11 feed conduit
12 discharge conduit
13 shut-off valve
14 shut-off valve
15 service water conduit
16 shut-off valve
17 pressure reduction valve
18 shut-off valve
19 sample container
20 discharge conduit
21 control and regulation unit
22 first switch
23 projection
24 second switch
25 bar
26 frame
27 grip part
28 end-part
29 end-part
30 upper disc
31 lower discs
32 weld seams
33 longitudinal rib
34 insertion direction
35 channel section
36 channel section
37 channel
38 web-like region
39 elastic material
40 ring seal
41 perpendicular through-beaming direction
42 marking

What is claimed is:

1. A device for detection of particles in a fluid, the device comprising:
    a receiver having a conduit for feeding the fluid, and a conduit for the discharge of the fluid;
    a light source;
    an optical sensor;
    a sample carrier, arranged between the light source and the optical sensor, for receiving fluid to be examined, wherein the sample carrier is movable relative at least to the sensor and is connectable via a fluid inlet to the conduit for feeding the fluid, and via a fluid outlet to the conduit for the discharge of the fluid, and wherein the sample carrier is exchangeably arranged in the receiver, the sample carrier comprising a closed channel formed between the fluid inlet and the fluid outlet conduit connections, the closed channel, at least in sections, comprising a transparent wall on two opposite sides;
    a pivotable bar arrangement for moving into a closed position fixing the sample carrier with a positive fit in a designated position in the receiver, the pivotable bar arrangement moving to an open position for withdrawal and replacement of the sample carrier with another sample carrier.

2. A device according to claim 1, further comprising a blocking devices for blocking at least one of the conduit for feeding the fluid and the conduit for the discharge of fluid.

3. A device according to claim 1, wherein the receiver comprises the conduit for feeding the fluid and the conduit for the discharge of fluid and each of the conduit for feeding the fluid and the conduit for the discharge of fluid extend from below the receiver into the sample carrier.

4. A device according to claim 1, wherein the light source and the optical sensor are arranged in a manner movable relative to the sample carrier in steps.

5. A device according to claim 1, wherein an optical axis formed between the light source and optical sensor is at an angle between 4° to 8° to a perpendicular through-beaming direction through the sample carrier.

6. A device according to claim 1, further comprising a position means provided between the receiver and the sample carrier only permitting a fluid conductive connection to at least one of the fluid inlet and the fluid outlet when the sample carrier is arranged in the designated position in the receiver.

7. A device according to claim 6, wherein the position means comprise a first switch which switches when the designated position of the sample carrier in the receiver is reached.

8. A device according to claim 1, wherein a positive-fit means is provided between the receiver and sample carrier for ensuring a designated arrangement of the sample carrier in the receiver.

9. A device according to claim 6, wherein the position means comprises:
   a first switch which switches when reaching the designated position of the sample carrier in the receiver; and
   a second switch which switches when the bar is in the position locking the sample carrier in the receiver.

10. A sample carrier for a device for detection of particles in a fluid, the device comprising a receiver, a light source, an optical sensor and the sample carrier, arranged between the light source and the optical sensor, for receiving fluid to be examined, wherein the sample carrier is movable relative at least to the sensor and is connectable via a fluid inlet to a conduit for feeding the fluid, and via a fluid outlet to a conduit for the discharge of fluid, the fluid inlet and the fluid outlet being arranged next to one another in an insertion direction, and wherein the sample carrier is exchangeably arranged in the receiver, wherein the sample carrier comprises a carrier frame which is closed off by transparent plates, with one of the transparent plates being at each of two sides, at least one of the transparent plates being arranged in a set-back manner with respect to a peripheral frame part, at least one channel-forming rib, which forms part of the carrier frame is provided between the fluid inlet and the fluid outlet, a projection at an insertion side, the projection being arranged out-of-center and forming a positive-fit means for positioning.

11. A sample carrier according to claim 10, wherein the carrier frame comprises a plastic injection molded part which is fixedly and sealingly connected to the transparent plates with a material fit by way of welding.

12. A sample carrier according to claim 10, wherein in the region of the inlets and outlets each comprise a recess in a portion of the frame part, each recess being filled with an elastic and seal-forming plastic.

13. A sample carrier according to claim 10, wherein the frame comprises a grip piece, which forms part of the frame, on one side.

14. A sample carrier according to claim 10, wherein the sample carrier has an essentially longitudinally extended and flat cuboid shape with flat sides with the transparent plates and with longitudinally extended sides arranged in an insertion direction.

15. A sample carrier according to claim 10, further comprising a closed channel formed between the fluid inlet and the fluid outlet conduit connections, the closed channel being on an inner side of the transparent walls and being provided with at least one of a coating and a surface structuring which prevents the formation of deposits.

16. A sample carrier according to claim 15, further comprising at least one marking provided between the transparent walls, on an inner side of the wall, in a region for an optical detection of the fluid.

17. A sample carrier according to claim 16, wherein the closed channel, in the region for the optical detection of the fluid, has a channel cross section with a width that is greater than a height, in a perpendicular through-beaming direction, and is 1.5 to 3 times as large.

18. A method for detecting particles in a fluid with a device comprising a receiver, a light source, an optical sensor and a sample carrier arranged between the light source and the optical sensor, for receiving fluid to be examined, wherein the sample carrier is movable relative at least to the sensor and is connectable via a fluid inlet to a conduit for feeding the fluid, and via a fluid outlet to a conduit for the discharge of fluid, and wherein the sample carrier is exchangeably arranged in the receiver, wherein the sample carrier comprises a carrier frame which is closed off by transparent plates, with one of the transparent plates being at each of two sides, the method comprising the steps of:
   bringing the sample carrier into a designated position in the device;
   introducing the fluid to be examined into the sample carrier via the feed conduit;
   shutting off the discharge conduit;
   closing the feed conduit after the build-up of pressure within the sample carrier;
   allowing a dwell time to pass and effecting the optical detection of the sample; and
   after the optical detection, the feed and discharge conduits are opened, whereupon the fluid located in the sample carrier is replaced and the cycle is repeated beginning with the step of shutting off the discharge conduit.

* * * * *